United States Patent [19]

DeLacy

[11] Patent Number: 4,634,868

[45] Date of Patent: Jan. 6, 1987

[54] NON-DESTRUCTIVE TESTING BY STIMULATED ELECTRON EMISSION CAPTURE

[75] Inventor: Thomas J. DeLacy, Los Altos, Calif.

[73] Assignee: Ford Aerospace & Communications Corporation, Detroit, Mich.

[21] Appl. No.: 682,642

[22] Filed: Dec. 17, 1984

[51] Int. Cl.⁴ .................................. G01N 23/04
[52] U.S. Cl. ................................ 250/306; 250/307; 378/63
[58] Field of Search ............ 250/306, 307, 308, 492.1, 250/492.3, 475.2, 492.24, 327; 378/54, 62, 63

[56] References Cited

U.S. PATENT DOCUMENTS

| | | | |
|---|---|---|---|
| 2,382,739 | 8/1945 | Müller | 250/311 |
| 2,417,110 | 3/1947 | Hillier | 250/307 |
| 2,523,306 | 9/1950 | Kaiser | 250/475.2 |
| 2,939,012 | 5/1960 | Scherbatskoy | 250/310 |
| 2,963,585 | 12/1960 | Beeh | 378/54 |
| 2,967,240 | 1/1961 | Koch | 204/130 |
| 3,428,803 | 2/1969 | Dyke et al. | 378/63 |
| 3,489,901 | 1/1970 | Brown | 250/308 |
| 3,758,778 | 9/1973 | Braunlich | 250/307 |
| 3,914,607 | 10/1975 | Cho et al. | 250/308 |
| 4,316,087 | 2/1982 | Yanaka et al. | 250/307 |
| 4,366,380 | 12/1982 | Mirkin | 250/307 |

Primary Examiner—Bruce C. Anderson
Assistant Examiner—Paul A. Guss
Attorney, Agent, or Firm—Edward J. Radlo; Clifford L. Sadler

[57] ABSTRACT

Non-invasive and non-destructive apparatus and method for imaging, recording, and comparing the mass density distributions and thicknesses of test specimens (19F, 19B). A source of medium-to-high-energy photons (3) directs a photon beam (4) at an electron source (17) comprised of high atomic number material, which emits in response thereto electrons (9F, 9B), some of which are not absorbed and not widely scattered by the test specimens (19F, 19B), but are transmitted therethrough and captured on one or more photographic films (15F, 15B) in contact with said specimens (19F, 19B). Net recorded film (15F, 15B) densities are in inverse relation to the mass density distribution of the corresponding test specimen (19F, 19B). A filter (5) is interposed between the photon source (3) and the capture film (15B) when back emission imaging (B) is employed. The filter (5) is optional when forward emission imaging (F) is used. The filter (5) absorbs photons (4) that have an energy sufficiently low to create an unwanted X-ray response on the capture film (15F, 15B) within the period required for the desired electron (9F, 9B) imaging.

11 Claims, 4 Drawing Figures

.25 CM

NON-DESTRUCTIVE TESTING BY STIMULATED ELECTRON EMISSION CAPTURE

TECHNICAL FIELD

This invention pertains to the field of non-destructive testing of materials by means of capturing electrons that have been stimulated into emission from an electron source by high energy photons.

BACKGROUND ART

In the field of industrial radiography, lead-foil screens are commonly used to generate secondary electron (photoelectron) emissions for intensification of the primary X-ray photon image. The photo electrons ejected from these screens do not interact with the test specimen. Emergent electrons, which act to increase the film response to changes in the intensity of the primary X-rays transmitted by the test specimen, are created by the interactions of the primary X-ray beam in the foil after having first traveled through the test specimen. The high specific ionization potential of electrons (about 100 times that of equivalent energy photons) increases the speed of radiography relative to a direct X-ray exposure without screens. Lead foil screens are also employed to reduce the influence of scatter, by absorbing secondary photons as well as electrons generated in the test specimen by the primary X-ray beam.

X-ray fluorescence and X-ray backscatter techniques have also been employed to study various materials and features, including the pattern of certain contamination defects and elemental compositions. In these processes, an X-ray signal is the primary objective of the analysis. In applications requiring film capture, various absorbers have been employed in these teachings to reduce the influence of electrons (Compton recoil and/or photoelectrons emitted from the specimen), which reduce the sharpness or contrast of the characteristic X-ray image. In the case of the subject invention, the X-rays 4 are deliberately hardened to desensitize the film 15F, 15B to the emergent X-ray beam 4, while recording the transmission of secondary electrons 9F, 9B passing through the test specimen 19F, 19B from an external target source 17.

Various means for producing an electron image have been reported in the prior art.

U.S. Pat. No. 3,758,778 discloses a technique in which low energy radiation, i.e., X-ray or infrared radiation, is used to trap electrons above the Fermi level at the surface of a test specimen. An electron microscope is used to accelerate and image the electrons to correlate to the surface features of the test specimen. The bombarding radiation source and secondary electron source are contained within the same vacuum envelope. In the present invention, on the other hand, an external medium-to-high-energy X- or gamma ray source 3 is used to eject a continuous spectrum of electrons 9F, 9B from the surface of a suitable target material 17 for imaging a detached test specimen 19F, 19B.

In the reference patent, the specimen temperature must be lowered below ambient in order to stabilize exothermic and/or exoelectron emission prior to creating a secondary surface emission by abruptly raising the specimen temperature above the Fermi level for exoelectron emission in response to the surface features, e.g., composition and topography, of the test specimen. In other words, the reference patent requires a controlled temperature environment. In the present invention, on the other hand, surface temperature is not a factor in creating an image of the uniformity and internal features of the test specimen 19F, 19B. The present invention does not require a controlled temperature environment.

In summary, the reference is a technique for recording surface features by stimulating electrons from within a test specimen; the electrons which contain the signal come from the specimen itself. On the other hand, the present invention records internal features at all points within the test specimen 19F, 19B using electrons 9F, 9B produced from a source 17 outside the test specimen 19F, 19B.

U.S. Pat. No. 2,967,240 discloses a method wherein surfaces of certain crystalline materials, e.g., piezoelectric monocrystals and dielectric crystals, are chemically etched in a caustic electrolyte while being simultaneously exposed to X-ray or electron beam radiation. An interface phenomenon acting to eject foreign ions from the electrolyte used for etching the crystals is observed spectroscopically. The pattern of interference is determined by the influence of flaws in the atomic crystalline structure, which flaws diffract the impinging radiation beam. Repeated or prolonged treatment may be used to reorder the crystalline lattice, thus eliminating the surface flaws. In the present invention, on the other hand, an etchant or external medium to sensitize or otherwise prepare the surface of the test specimen 19F, 19B for testing is not required or used. The present invention is not limited to recording an image of the crystalline state of the test specimen 19F, 19B.

In summary, the reference is a method which is sensitive to defects on or immediately below the surface of the test specimen. It employs spectroscopic analysis to reveal impurities in the specimen surface. On the other hand, the present invention is sensitive to defects throughout the test specimen 19F, 19B; internal impurities are revealed by direct imaging on a photographic plate 15F, 15B. The reference method employs low energy radiation bombardment from a discrete energy 50 Kev to 60 Kev source. The present invention employs medium-to-high-energy radiation bombardment 4, 7, and is not limited to a discrete energy photon source 3.

U.S. Pat. No. 2,939,012 describes nondestructive means whereby a beam of high energy electrons of known energy distribution is directed at the surface of an unknown test specimen. A photomultiplier crystal detector is used to measure the number of secondary electrons scattered at discrete energy levels as a function of the elemental composition of the specimen. The present invention, on the other hand, employs a capture film 15F, 15B which responds to electron particles which are transmitted (not absorbed and not widely scattered) by the specimen 19F, 19B, rather than scattered radiation; and the energy profile of the photon source 3 used to produce the electrons does not have to be known.

The reference employs a crystal detector to record backward scatter response; employs electron beam bombardment as a primary incident radiation source; and does not produce an image. The present invention uses a photographic film detector 15F, 15B to record forward or back emission electron 9F, 9B transmission response; and employs an X-ray or gamma ray source 3 as a primary particle stimulation source.

Secondary references are U.S. Pat. Nos. 2,382,739; 2,417,110; 4,316,087; and 4,366,380.

DISCLOSURE OF INVENTION

The present invention is a non-invasive and hence non-destructive apparatus and method for imaging and permanently recording the mass density distribution of one or more test specimens (19F, 19B), offering improved sensitivity and improved resolution of defects. An external source (3) is used to direct a medium-to-high-energy photon beam (4) to interact with a suitable high atomic number material electron source (17) which emits, in response to this stimulation, preferably planar beams of electrons (9F, 9B). Emergent electrons (9F, 9B) which are not absorbed or widely scattered by the test specimens (19F, 19B) are transmitted therethrough and captured on photographic film (15F, 15B). Within measurable and qualified thickness bounds (electron particle range), the density of the image recorded on the film (15F, 15B) is in inverse relationship to the mass density distribution of the corresponding test specimen (19F, 19B, respectively).

When back emission imaging (B) is employed, a filter (5) is interposed between the photon source (3) and the capture film (15B) for absorbing low energy photons (4) to which the film (15B) is highly sensitive, thereby maximizing the contrast of the electron image on the film (15B). The use of the filter (5) is optional when forward emission imaging (F) is employed in lieu of back emission imaging (B).

All the above-described items except for the photon source (3) and the filter (5) are preferably enclosed within a light-proof vacuum cassette (13) fabricated of a material having a low atomic number.

BRIEF DESCRIPTION OF THE DRAWINGS

These and other more detailed and specific objects and features of the present invention are more fully disclosed in the following specification, reference being had to the accompanying drawings, in which.

BEST MODE FOR CARRYING OUT THE INVENTION

Figure 1:
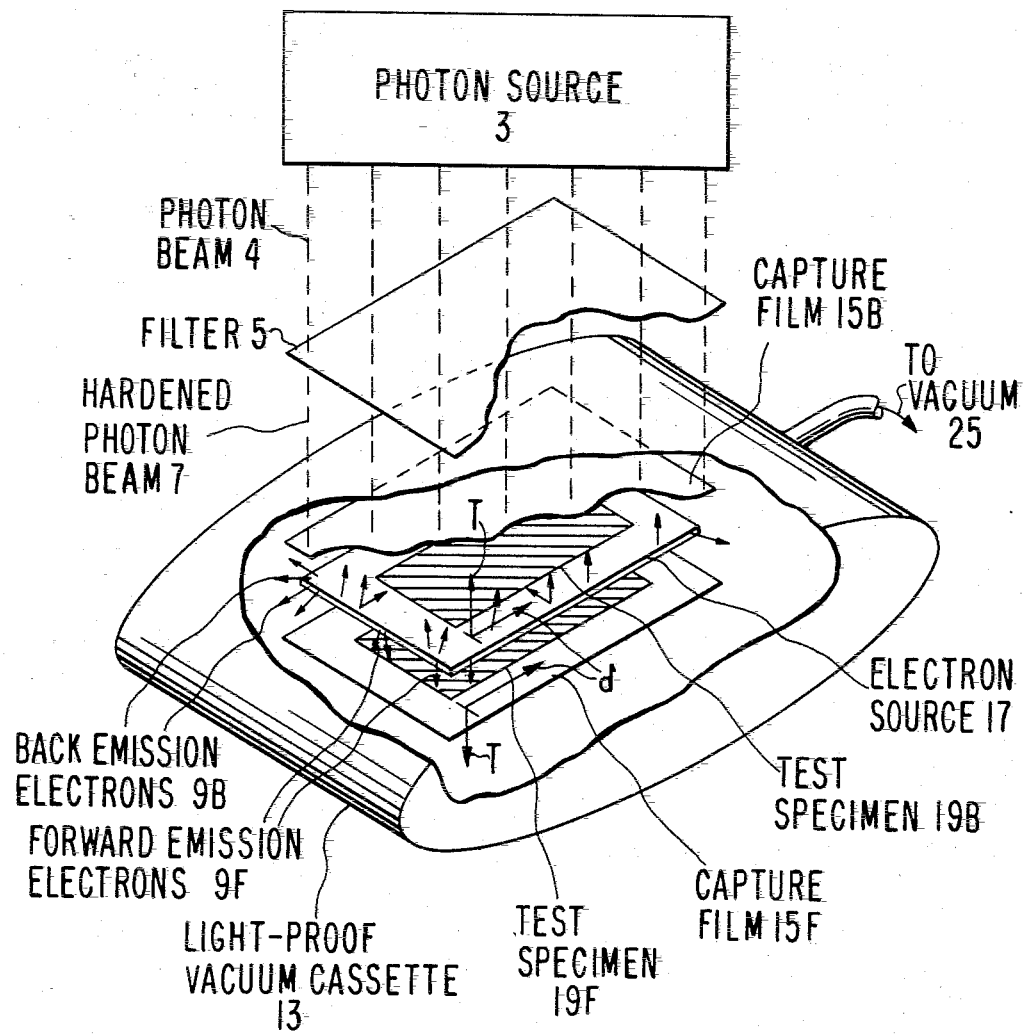
FIG. 1 is a partially broken-away exploded sketch showing the apparatus of a preferred embodiment of the present invention.

Photon source 3 is a source which produces a medium-to-high-energy beam of photons 4. Three suitable sources 3, which were used during the testing of this invention, are: a Norelco isotropic source of X-rays having a continuous range of energy up to a peak of 300 Kev; an isotropic gamma ray source from an irridium 192 isotope having a spectrum up to about 600 Kev; and an isotropic gamma ray source from a cobalt 60 isotope having an effective monochromatic energy of about 1 Mev. It is not desirable for source 3 to emit radiation at energies much greater than 1 Mev because such high energy photons would produce positron/electron pairs upon interacting with electron source 17, wasting energy. Also, the resulting annihilation radiation would be a source of unfiltered photons, reducing the contrast of the electron 9F, 9B signal captured by films 15B, 15F.

The beam 4 is directed at electron source 17, a material having a high atomic number (Z), so that electrons 9F, 9B emitted by source 17 in response to the stimulation from photons 4, 7 will originate from near the surface of source 17 (electrons 9F, 9B released from substantially below the surface of source 17 will be absorbed by source 17 itself). Because all electrons 9F, 9B used in imaging originate very close to the surface of the corresponding test specimen 19F, 19B, respectively, the uniformity of the captured image is enhanced.

Suitable materials for electron source 17 are niobium, uranium, or tantalum, which offer surface rigidity as well as a high Z. Source 17 may be planar as illustrated or curved to conform to a curved test specimen 19F, 19B. Source 17 is made thin so that sufficient photons 4, 7 can penetrate to the far side of the plate 17 to enable forward imaging (F) as well as back imaging (B). Throughout this specification and drawings, the letter F after a reference numeral designates the forward direction, i.e., the direction following any vector pointing away from the photon source 3. The letter B after a reference numeral designates the back direction, i.e., the direction following any vector pointing towards the photon source 3.

Compton recoil and/or photoelectrons 9F, 9B are emitted from the forward and back surfaces, respectively, of electron source 17 in response to the incident radiation 4, 7. If the electron source 17 is planar, as preferable and as illustrated in FIG. 1, the overall shape of each electron beam 9F, 9B is planar although the individual electrons 9F, 9B travel in random directions. The most energetic electrons are 9F electrons that are orthogonal to source 17; those in the plane of source 17 are self-absorbed. The effective energy range of electrons 9F, 9B is between zero and the maximum energy of the impinging photons 4 or 7, since the emergent electrons 9F, 9B come from various near-surface depths and angles in the electron source 17.

Each capture film 15F, 15B is a photographic emulsion film capable of recording an image in response to incident electrons 9F, 9B. The density (amount of darkening) of the recorded image is proportional to the exposure of the electrons 9F, 9B, that are transmitted (i.e., not absorbed and not widely scattered) by the corresponding test specimen, 19F, 19B, since it is these transmitted electrons 9F, 9B which impinge upon the film 15F, 15B. Exposure equals the time during which the transmitted electrons 9F, 9B strike the capture film 15F, 15B multiplied by the intensity of the incident electron 9F, 9B radiation. The recorded film density can be measured by an optical denstiometer as the base 10 logarithm of the inverse of the transmitted incident diffuse light. The film 15F, 15B density is inversely proportional to the mass density distribution of the corresponding area of the test specimen 19F, 19B, because the test specimen 19F, 19B absorbs and widely scatters incident electrons in proportion to its mass density at said area.

Film 15F, 15B can be a standard photographic negative emulsion having as an active ingredient a silver halide, e.g., silver bromide. When the film 15F, 15B has an emulsion side and a substrate side, the emulsion side should face the test specimen 19F, 19B. Examples of suitable films 15F, 15B are Eastman Kodak type single emulsion R and type positive photographic emulsion. Film 15F, 15B is highly sensitive to low energy X- and gamma rays, i.e., those having an energy of less than about 200 Kev, while being relatively insensitive to medium and high energy X- and gamma rays, i.e., those having an energy of greater than about 200 Kev. The contrast (change in density divided by density) of the recorded images can be changed by varying the emulsion thickness of the films 15F, 15B and/or by changing the energy distribution of photon source 3 thus changing the capture distance or range of the stimulated electrons 9F, 9B. Very high energy electrons 9F, 9B may travel through film 15F, 15B without being trapped, producing no apparent signal contrast when recorded. Lower energy electrons 9F, 9B give up energy continuously as they are absorbed by the film 15F, 15B. Differences in relative film 15F, 15B ionization, correlating to specimen 19F, 19B thickness and/or mass density changes, may be observed when using said lower energy electrons 9F, 9B.

Filter 5 is optional when just forward emission (F) is used, but is mandatory when back emission (B) is used. The purpose of filter 5, which is made of a high atomic number material such as lead (Pb), is to absorb low-energy photons 4, i.e., those photons 4 having an energy below about 200 Kev, because said photon 4 would otherwise darken film 15B, 15F, preventing or severely reducing signal contrast; for forward emission (F) imaging, this shielding is performed by electron source 17.

The image captured on the film 15F, 15B is a two-dimensional image of the corresponding abutting area of the specimen 19F, 19B. A three-dimensional image of specimen 19F, 19B can be obtained by thinly slicing the specimen 19F, 19B and stacking the resulting two-dimensional images.

Vacuum cassette 13 contains electron source 17, specimens 19F, 19B, and capture films 15F, 15B. Cassette 13, which is evacuated by means of a vacuum pump 25, sandwiches the within-contained items so as to eliminate unwanted diffusion and absorption of the emergent electrons 9F, 9B, and resulting loss of image quality. Since it is desirable to prevent unwanted exposure of films 15F, 15B by ambient light, cassette 13 should be made from or coated with a material that is opaque to such light. Cassette 13 should be made of a low atomic number material to prevent further filtering of the hardened photon beam 4, and so that any X-rays or secondary electrons given off by cassette 13 will be minimized to preclude unwanted darkening of films 15F, 15B.

Figure 3:
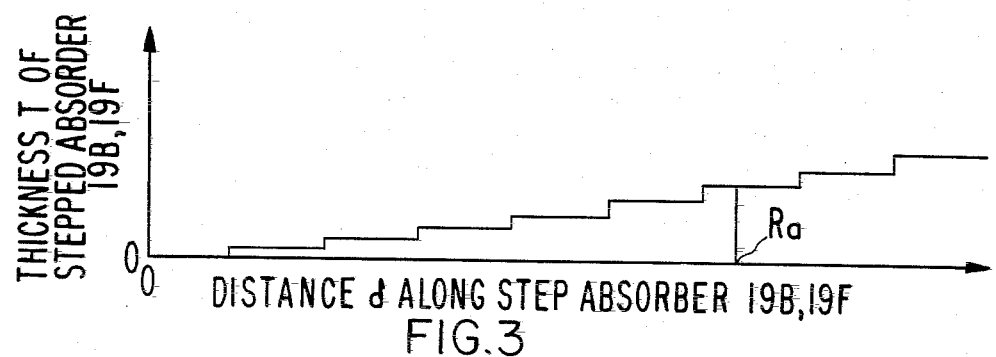
FIG. 3 shows the approximate geometrical shape, not to scale, of each stepped absorber 19F, 19B imaged in FIG. 2.

Tables I through IV reproduced below show the forward (F) and back (B) emission images recorded on capture films 15F and 15B using a 300 Kev heavily filtered X-ray source 3. Test objects 19F and 19B consisted of aluminum and Mylar step tablets, illustrated in FIG. 3, used to determine the nature of emergent radiation from electron source 17 and effective range of electrons 9F, 9B for technique development and calibration. The flat (unstepped) sides of the stepped absorbers 19F, 19B were placed facing the corresponding film 15F, 15B. The data of Tables I and III were generated in a first experiment, and the data of Tables II and IV were generated in a second experiment.

TABLE I

FORWARD EMISSION (F)
Mylar step absorber 19F

| Step No. | g/cm² along T | Film 15F Density | Relative Transmittance |
|---|---|---|---|
| 0 | 0 | 3.40 | 1.0 |
| 1 | 3.3 | 2.58 | 0.758 |
| 2 | 6.6 | 2.32 | 0.682 |
| 3 | 10 | 2.19 | 0.644 |
| 4 | 13.2 | 2.13 | 0.626 |
| 5 | 16.5 | 2.09 | 0.615 |
| 6 | 19.8 | 2.04 | 0.597 |
| 7 | 23.1 | 2.01 | 0.591 |
| 8 | 26.4 | 2.01 | 0.591 |

TABLE II

FORWARD EMISSION (F)
aluminum step absorber 19F

| Step No. | g/cm² along T | Film 15F Density | Relative Transmittance |
|---|---|---|---|
| 0 | 0 | 3.40 | 1.0 |
| 1 | 4.5 | 2.19 | 0.644 |
| 2 | 9 | 1.89 | 0.555 |
| 3 | 13.5 | 1.79 | 0.526 |
| 4 | 18.0 | 1.75 | 0.515 |
| 5 | 22.5 | 1.75 | 0.515 |

TABLE III

BACK EMISSION (B)
Mylar step absorber 19B

| Step No. | g/cm² along T | Film 15B Density | Relative Transmittance |
|---|---|---|---|
| 0 | 0 | 1.87 | 1.0 |
| 1 | 3.3 | 1.35 | 0.72 |
| 2 | 6.6 | 1.29 | 0.69 |
| 3 | 10 | 1.27 | 0.68 |
| 4 | 13.2 | 1.25 | 0.67 |
| 5 | 16.5 | 1.24 | 0.66 |
| 6 | 19.8 | 1.24 | 0.66 |

TABLE IV

BACK EMISSION (B)
aluminum step absorber 19B

| Step No. | g/cm² along T | Film 15B Density | Relative Transmittance |
|---|---|---|---|
| 0 | 0 | 1.81 | 1.0 |
| 1 | 4.5 | 1.27 | 0.70 |
| 2 | 9 | 1.24 | 0.69 |
| 3 | 13.5 | 1.23 | 0.68 |
| 4 | 18.0 | 1.23 | 0.68 |

The second column of each of Tables I–IV tabulates the mass in the absorber 19F, 19B along the T (thickness) dimension (see FIG. 1; T is orthogonal to the common planes of items 15F, 15B, 19F, 19B, and 17) per unit area orthogonal to T. Values of film 15F, 15B density tabulated above in the third column of each Table were as measured using a transmission densitometer, without correction for recorded background radiation or chemical fog. Entries in each fourth column are normalized values of the corresponding third column entry.

Figure 2:
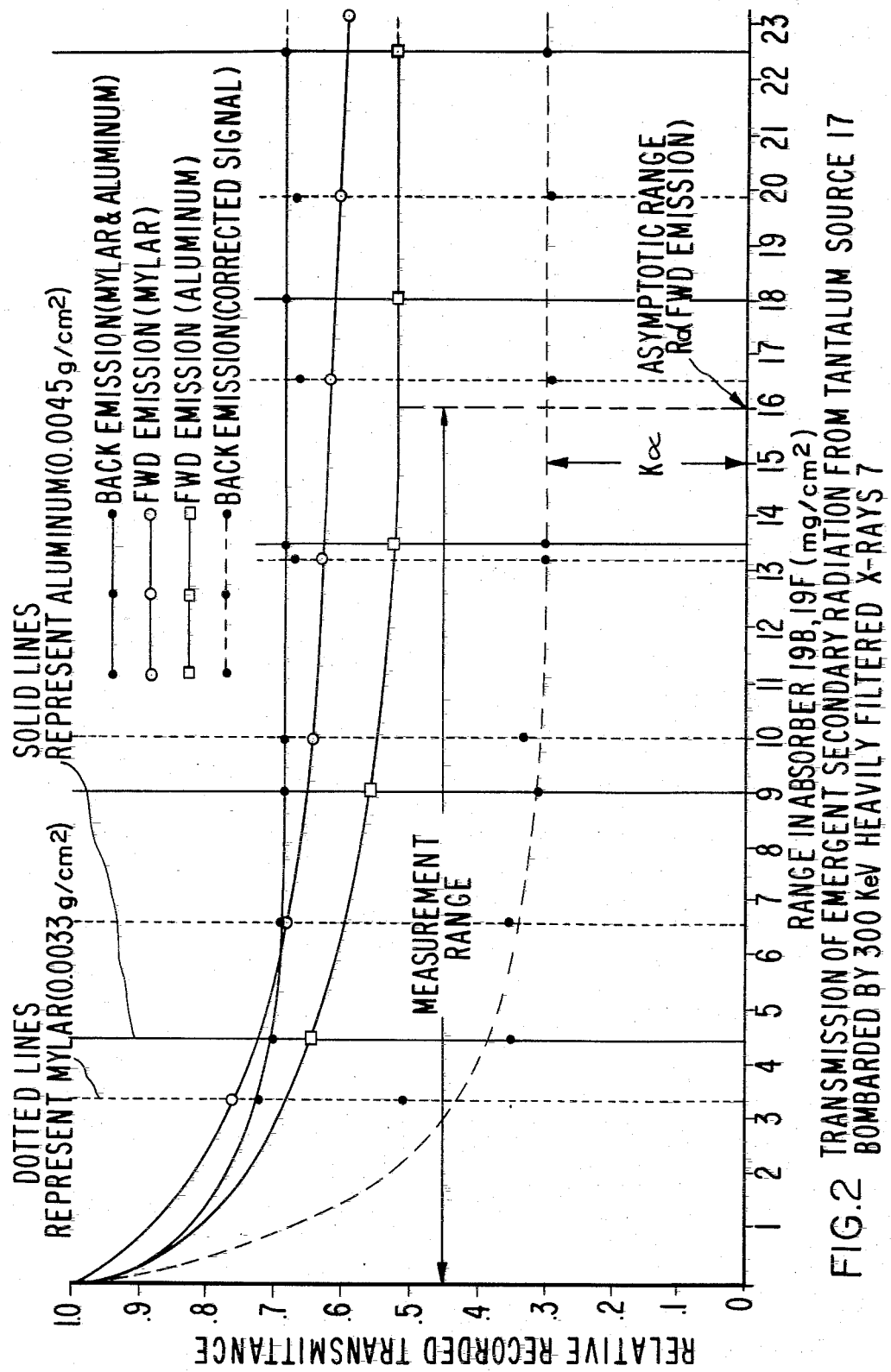
FIG. 2 is a graph showing electron 9F, 9B transmittance recorded on capture films 15F, 15B for Mylar and aluminum stepped absorbers 19F, 19B used for calibration.

FIG. 2 illustrates in graphic form, by means of the three solid curves, the data tabulated in the fourth columns of Tables I–IV. A zero thickness for absorbers 19F, 19B is represented at the left hand sides of FIGS. 2 and 3, whose x-axes correspond; thickness increases as one moves to the right on said Figs. For FIG. 2, the x-axis dimension has been recast as the effective range of the electrons 9F, 9B in the corresponding absorber 19F, 19B, in units of mg of the absorber's mass per cm² orthogonal to T.

Aluminum and Mylar were selected for these calibration experiments because they have the same mass density but different atomic number Z. The back emission (B) data for the two materials 19B was so identical that a single curve was drawn linking both sets of data points. For forward emission (F), two curves were drawn, although the data points for the two materials 19F were close. The fact that the FIG. 2 curves are alsmost identical shows that the radiation being recorded is electron radiation, not X-ray or gamma ray radiation, because electron absorption and scatter is a function of the mass density distribution of a material 19F, 19B while X-ray and gamma ray absorption and scatter are functions of the atomic number of the material 19F, 19B.

FIG. 2 shows that after the absorbers 19F, 19B reach a certain thickness corresponding to an asymptotic range Ra, the relative recorded transmittance on the corresponding capture film 15F, 15B no longer decreases; the curve becomes horizontal at this point. This implies that even when the absorber 19F, 19B is absorbing or widely scattering all the electrons 9F, 9B, there is still some radiation causing a developer rection on the capture film 15F, 15B. This asymptotic amount of darkening is (1) primarily due to X-ray emission from the electron source 17 and elsewhere, and to the minor influence of chemical fog; and (2) slightly lower for forward emission films 15F than for back emission films 15B, because of self-absorbtion within electron source 17. Once this asymptotic amount has been subtracted from the recorded relative transmittance or film density measurements for two test specimens (two 19F's, two 19B's, or a 19F and a 19B, a different amount being subtracted out for the forward direction as for the back direction), the ratio of net recorded transmittance or net film density for the two specimens 19F, 19B is equal to the inverse of the ratio of their mass densities, for any equally-sized area within the planes of the specimens 19F, 19B.

The bottom, dotted curve in FIG. 2 illustrates the data of the back emission curve, after recorded transmittance due to infiltered X-rays from source 3 has been subtracted out. The amount of this transmittance is time-dependent, and was determined by extending the planar area of capture film 15B beyond the confines of absorber 19B. An amount of asymptotic transmittance Kα still remains in the dotted curve, and is attributable to X-rays emitted by electron source 17 in response to the bombardment from the photon source 3 and to minor chemical fog.

FIG. 2 can be used to determine whether the thickness of a specimen 19F, 19B is such as to render it possible to use the apparatus and method of the present invention to record a two-dimensional image corresponding to the mass density distribution throughout the plane of the specimen 19F, 19B. This condition is equivalent to the condition that the recorded relative transmittance is within the non-horizontal portion of a FIG. 2 type curve. FIG. 2 can also be used to qualify materials by thickness, e.g., by determining whether the thickness of any given test specimen 19F, 19B is beyond the range of electrons 9F, 9B, such that its recorded relative transmittance is effectively zero or falls within the horizontal portion of its FIG. 2 curve.

Figure 4:
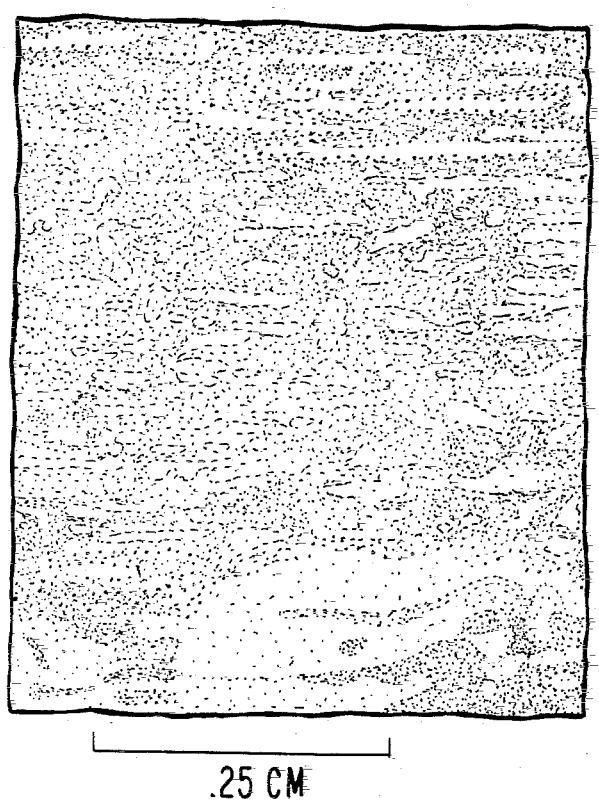
FIG. 4 is an artist's rendition of a negative of a stimulated electron 9B emission capture image for a typical test specimen 19B produced by the instant invention.

FIG. 4 is an artist's reproduction of the back-emission (B) response of a 15 mil thick (20 to 35 mg/cm²) graphite-fiber/solvent diluted, resin-matrix prepreg specimen 19B imaged in the uncured state. The image was produced on Eastman Kodak type R-1 single-emulsion film 15B using a 1 Mev cobalt 60 gamma-ray source 3 at a distance of 1 meter from the test specimen 19B. Higher film 15B density is indicated by more closely spaced dots. FIG. 4 represents the film density distribution observed when the developed image was printed on photographic paper; the response represented on FIG. 4 is a "negative" compared with the "positive" illustrated in FIG. 2. Accordingly, the darker areas represent increased mass density within corresponding areas of specimen 19B, indicating greater solvent penetration. The dotted horizontal lines in FIG. 4 represent the graphite fibers in test specimen 19B.

The back emission electrons 9B have a lower spectral energy component distribution than the forward emission electrons 9F, because of the kinematics of photon/electron interactions within source 17, and because photons 4, 7 that travel all the way through source 17 to trigger forward electrons 9F have to be, on average, more energetic than those triggering back electrons 9B on the near surface of plate 17. As a consequence, back imaging (B) provides more contrast while forward imaging (F) can image thicker test specimens 19F.

Electrons emitted from the specimen 19F, 19B itself usually have an insignificant effect on the recorded image, because the specimen 19F, 19B usually has a low Z. When the specimen 19F, 19B contains high Z additives, the recorded image must be interpreted accordingly.

In instances where a given test specimen 19F, 19B, e.g., an uncured, resin-matrix composite, contains volatile materials such as solvents, which may be depleted by evaporation, and/or where the surface of the test specimen 19F, 19B exhibits tack or adhesive-like properties, it is desirable to place a thin-film barrier between the capture emulsion 15F, 15B and said test specimen 19F, 19B surface, to protect the emulsion 15F, 15B during testing and to reduce the level of potential evaporation. A 0.25 mil thick aluminized Mylar barrier has been successfully used for this purpose in conjunction with prepreg materials 19F, 19B ranging to about 20 mils thick (20 to 40 mg/cm²). However, the effective range and sharpness of the recorded image is reduced by use of such a barrier. Electron 9F, 9B absorption by any such interposed protective barrier must be considered when selecting the suitable photon source 3, so that the imaging electrons 9F, 9B may pass through the test specimen 19F, 19B with sufficient remaining energy to also penetrate the barrier material. An analysis of emergent electron particles 9F, 9B developed using iridium 192 gamma-ray isotope bombardment having an effective energy of 600 Kev showed that the electrons 9F, 9B had an asymptotic range Ra of about 40 mg/cm². By way of comparison, the asymptotic range Ra of electrons 9B used to produce the image illustrated in FIG. 4 was determined to be between 60 mg/cm² and 80 mg/cm².

The stimulated electron 9F, 9B imaging of the present invention offers the advantages with respect to X-ray or gamma-ray imaging that:

(1) For the same energy level and distance of travel, an electron has a much higher specific ionization potential than does a photon; therefore, the electron is a more sensitive imager;

(2) Unlike the case with X-rays, which lose intensity but not energy as they travel through a given absorber, the thickness of the capture film 15F, 15B can be varied to vary the contrast of the recorded image; and (3) Assuming that the energy of the electrons from source 17 is controlled by selecting or regulating photon source 3 such that the emergent electrons 9F, 9B are substantially stopped within the imaging emulsion layer of the capture film 15F, 15B (rather than being captured by the film's supporting substrate, which, if present, should face away from electron source 17), higher ionization at the end of the path of the electron 9F, 9B will enhance the response due to subtle mass density or thickness changes of the test specimen 19F, 19B.

The above description is included to illustrate the operation of the preferred embodiments and is not meant to limit the scope of the invention. The scope of the invention is to be limited only by the following claims. From the above discussion, many variations will be apparent to one skilled in the art that would yet be encompassed by the spirit and scope of the invention. For example, many test specimens 19F and/or 19B can be positioned side-by-side on the same surface of source 17.

What is claimed is:

1. Apparatus for recording the mass density distribution of a first test specimen, said apparatus comprising:
   means for emitting a medium-to-high-energy beam of photons;
   an electron source disposed to receive the photon beam and generate in response thereto a stimulated beam of emergent electrons generally oriented to interrogate said test specimen; and
   a first capture film disposed to record emergent electrons that are transmitted through the test specimen; wherein
   the test specimen is sandwiched between the electron source and the capture film, and absorbs and scatters some of the electrons in the electron beam, wherein the electrons not absorbed and not widely scattered by the test specimen produce on the capture film an image that is representative of the mass density distribution of the test specimen.

2. The apparatus of claim 1 further comprising a filter positioned between the photon emitting means and the capture film, wherein the filter absorbs photons that have an energy sufficiently low to produce an image on the capture film, whereby said low energy photons are inhibited from darkening the capture film.

3. The apparatus of claim 1 further comprising:
   a second capture film sensitive to incident electrons; and
   a second test specimen, sandwiched between the second capture film and the electron source, wherein the second capture film records an image of electrons that are not absorbed and not widely scattered by the second test specimen, said image being a representation of the mass density distribution of the second test specimen; wherein
   one of said first and second test specimens and its corresponding capture film are positioned between the photon emitting means and the electron source, and are therefore responsive to back emission electrons; and
   the other of said first and second test specimens and its corresponding capture film are positioned on a side of the electron source facing away from the photon emitting means, and are therefore responsive to forward emission electrons.

4. The apparatus of claim 1 wherein the electron source is a flat plate fabricated of a high atomic number material.

5. The apparatus of claim 1 wherein the electron source is fabricated from the class of materials comprising tantalum, niobium, and uranium.

6. The apparatus of claim 1 wherein the electron source, test specimen, and capture film are enclosed in a low atomic number vacuum cassette that is opaque to ambient light.

7. Apparatus of claim 1 further comprising a calibration specimen in the form of a step-tablet of known material and having a series of graded thickness layers transcending the range of electrons emergent from said electron source; wherein
   the calibration specimen is sandwiched between the electron source and the capture film but is not stacked with respect to the test specimen, and absorbs and scatters some of the electrons in the beam, such that electrons not absorbed and not widely scattered by said calibration specimen ionize the capture film in relation to the mass density of said graded thickness layers, for comparison to the response of said capture film to the test specimen.

8. Method for measuring the mass density of a test specimen, said method comprising the steps of:
   sandwiching said test specimen and a calibration specimen, said calibration specimen having a known mass density, between an electron source fabricated of a material having a high atomic number and a capture film sensitive to incident electrons in such a way that the test specimen and calibration specimen are not stacked with respect to each other;
   bombarding the specimens, electron source, and film with medium-to-high-energy photons;
   recording, on the film, densities of exposure attributable to trapped electrons originating from the source and stimulated into emission as a result of the photon bombardment, said stimulated electrons having passed through the specimens and exposed the film;
   subtracting, from the recorded film densities of the previous step, densities attributable to X-ray and chemical fog darkening of the film, so as to obtain net film densities corresponding to each of the test specimen and the calibration specimen; and
   measuring the mass density of the test specimen on the basis of its being substantially equal to the net film density corresponding to the calibration specimen multiplied by the mass density of the calibration specimen divided by the net film density corresponding to the test specimen.

9. A method for comparing the mass density distributions of first and second test specimens, said method comprising the steps of:
   sandwiching each test specimen between an electron source fabricated of a material having a high atomic number and a capture film sensitive to incident electrons in such a way that the test specimens are not stacked with respect to each other;
   bombarding the specimens, electron source, and film(s) with medium-to-high-energy photons;
   recording, on the film(s), densities of exposure attributable to trapped electrons originating from the source and stimulated into emission as a result of the photon bombardment, said stimulated electrons having passed through the specimens and exposed the film(s);

subtracting, from the two recorded fiml densities of the previous step, film densities attributable to X-ray and chemical fog darkening of the film(s), so as to obtain two net film densities; and comparing the mass density distributions of the specimens on the basis of their being substantially inversely proportional to said two net film densities of the previous step.

10. Apparatus for measuring the thickness of a test specimen, said apparatus comprising:

means for emitting a medium-to-high-energy beam of photons;

an electron source disposed to receive the photon beam and to generate in response thereto a stimulated beam of emergent electrons generally oriented to interrogate said test specimen; and a capture film disposed to record electrons transmitted by said test specimen; wherein the test specimen is sandwiched between the electron source and the capture film, and absorbs and scatters some of the electrons in the emergent electron beam, wherein the electrons not absorbed and not widely scattered by the test specimen ionize the capture film in relation to the thickness of said specimen acting to absorb and widely scatter electrons which may otherwise be transmitted to expose said capture film;

said apparatus further comprising a calibration specimen in the form of a step tablet of known material and having a series of graded thickness layers transcending the range of electrons emergent from said electron source; wherein the calibration specimen is sandwiched between the electron source and the capture film but is not stacked with respect to the test specimen, and absorbs and scatters some of the electrons in the beam, such that electrons not absorbed and not widely scattered by the calibration specimen ionize the capture film in relation to the thickness of said graded thickness layers, for comparison to the response of said capture film to the test specimen.

11. A method for measuring the thickness of a test specimen, said method comprising the steps of:

sandwiching a test specimen and a calibration specimen, the calibration specimen having a known thickness and the same mass density as the test specimen, between an electron source fabricated of a material having a high atomic number and a capture film sensitive to incident electrons in such a way that the test specimen and calibration specimen are not stacked with respect to each other;

bombarding the specimens, electron source, and film with medium-to-high-energy photons;

recording, on the film, densities of exposure attributable to trapped electrons originating from the source and stimulated into emission as a result of the photon bombardment, said stimulated electrons having passed though the specimens and exposed the film;

subtracting, from the recorded film densities of the previous step, densities attributable to X-ray and chemical fog darkening of the film, so as to obtain net film densities corresponding to each of the test specimen and calibration specimen; and measuring the thickness of the test specimen on the basis of its being substantially equal to the known thickness of the calibration specimen multiplied by the net film density corresponding to the calibration specimen divided by the net film density corresponding to the test specimen.

* * * * *